(12) United States Patent
Johnson (10) Patent No.: US 8,668,687 B2
(45) Date of Patent: Mar. 11, 2014

(54) SYSTEM AND METHOD FOR REMOVING MEDICAL IMPLANTS

(75) Inventor: Kristin D. Johnson, Louisville, CO (US)

(73) Assignee: Covidien LP, Mansfield, MA (US)

( * ) Notice: Subject to any disclaimer, the term of this patent is extended or adjusted under 35 U.S.C. 154(b) by 788 days.

(21) Appl. No.: 12/845,842

(22) Filed: Jul. 29, 2010

(65) Prior Publication Data
US 2012/0029506 A1 Feb. 2, 2012

(51) Int. Cl.
*A61B 18/18* (2006.01)
*A61N 1/00* (2006.01)
*A61B 19/00* (2006.01)

(52) U.S. Cl.
USPC .............................. 606/41; 607/122; 128/898

(58) Field of Classification Search
USPC ........... 128/898; 606/20–82, 108; 604/22, 25; 607/122, 126, 128
See application file for complete search history.

(56) References Cited

U.S. PATENT DOCUMENTS

| | | | |
|---|---|---|---|
| 3,434,476 A | 3/1969 | Shaw et al. |
| 3,838,242 A | 9/1974 | Goucher |
| 3,938,525 A | 2/1976 | Coucher |
| 3,991,764 A | 11/1976 | Incropera et al. |
| 4,781,175 A | 11/1988 | McGreevy et al. |
| 5,088,997 A | 2/1992 | Delahuerga et al. |
| 5,217,457 A | 6/1993 | Delahuerga et al. |
| 5,554,172 A | 9/1996 | Horner et al. |
| 5,669,904 A | 9/1997 | Platt, Jr. et al. |
| 5,669,907 A | 9/1997 | Platt, Jr. et al. |
| 5,707,402 A | 1/1998 | Heim |
| 5,720,745 A | 2/1998 | Farin et al. |
| 6,099,523 A | 8/2000 | Kim et al. |
| 6,149,620 A | 11/2000 | Baker et al. |
| 6,159,531 A | 12/2000 | Dang et al. |
| 6,172,130 B1 | 1/2001 | Bellesort |
| 6,183,469 B1 | 2/2001 | Thapliyal et al. |
| 6,197,026 B1 | 3/2001 | Farin et al. |

(Continued)

FOREIGN PATENT DOCUMENTS

| | | |
|---|---|---|
| DE | 3710489 | 11/1987 |
| DE | 4139029 | 6/1993 |

(Continued)

OTHER PUBLICATIONS

U.S. Appl. No. 08/383,162, filed Feb. 3, 1995.

(Continued)

*Primary Examiner* — Bill Thomson
*Assistant Examiner* — Nathan J Jenness (57) ABSTRACT

A method for removing a medical implant is contemplated by the present disclosure. The method includes the steps of guiding a plasma device to an implantation site. The plasma device includes a catheter having a catheter shaft. The catheter shaft includes a proximal portion and a flexible distal portion and a lumen defined therein terminating in an opening proximate a distal end thereof. The lumen is in fluid communication with an ionizable media source. The plasma device also include one or more electrodes proximate the opening and adapted to couple to a power source. The method also includes the steps of positioning the opening proximate a medical implant, supplying ionizable media to the opening, energizing the electrode to ignite the ionizable media to form a plasma plume emanating from the opening and manipulating the plasma plume relative to the medical implant to remove tissue surrounding the medical implant.

7 Claims, 6 Drawing Sheets

(56) References Cited

U.S. PATENT DOCUMENTS

| | | |
|---|---|---|
| 6,206,878 B1 | 3/2001 | Bishop et al. |
| 6,213,999 B1 | 4/2001 | Platt, Jr. et al. |
| 6,225,593 B1 | 5/2001 | Howieson et al. |
| 6,264,650 B1 | 7/2001 | Hovda et al. |
| 6,348,051 B1 | 2/2002 | Farin et al. |
| 6,379,351 B1 | 4/2002 | Thapliyal et al. |
| 6,475,217 B1 | 11/2002 | Platt |
| 6,558,383 B2 | 5/2003 | Cunningham et al. |
| 6,565,558 B1 | 5/2003 | Lindenmeier et al. |
| 6,666,865 B2 | 12/2003 | Platt |
| 6,780,178 B2 | 8/2004 | Palanker et al. |
| 6,852,112 B2 | 2/2005 | Platt |
| 6,890,332 B2 | 5/2005 | Tuckai et al. |
| 6,911,029 B2 | 6/2005 | Platt |
| 6,958,063 B1 | 10/2005 | Soll et al. |
| 7,122,035 B2 | 10/2006 | Canady |
| 7,311,708 B2 | 12/2007 | McClurken |
| 7,316,682 B2 | 1/2008 | Konesky |
| 7,361,175 B2 | 4/2008 | Suslov |
| 7,445,619 B2 | 11/2008 | Auge, II et al. |
| 7,458,973 B2 | 12/2008 | Ouchi |
| 7,549,990 B2 | 6/2009 | Canady |
| 7,572,255 B2 | 8/2009 | Sartor et al. |
| 7,578,817 B2 | 8/2009 | Canady |
| 7,578,818 B2 | 8/2009 | Platt |
| 7,601,150 B2 | 10/2009 | Farin |
| 7,608,839 B2 | 10/2009 | Coulombe et al. |
| 7,628,787 B2 | 12/2009 | Sartor et al. |
| 7,648,503 B2 | 1/2010 | Podhajsky |
| 7,691,102 B2 | 4/2010 | Podhajsky et al. |
| 2002/0022836 A1 | 2/2002 | Goble et al. |
| 2002/0022838 A1 | 2/2002 | Cunningham et al. |
| 2003/0008327 A1 | 1/2003 | Ornatskaia |
| 2003/0093073 A1 | 5/2003 | Platt |
| 2003/0105456 A1 | 6/2003 | Lin |
| 2003/0125727 A1* | 7/2003 | Truckai et al. ............ 606/41 |
| 2003/0208194 A1 | 11/2003 | Hovda et al. |
| 2004/0116918 A1 | 6/2004 | Konesky |
| 2004/0138658 A1 | 7/2004 | Farin et al. |
| 2004/0181220 A1 | 9/2004 | Farin |
| 2005/0080413 A1 | 4/2005 | Canady |
| 2005/0107786 A1 | 5/2005 | Canady |
| 2006/0004354 A1 | 1/2006 | Suslov |
| 2006/0036239 A1 | 2/2006 | Canady |
| 2006/0052771 A1 | 3/2006 | Sartor et al. |
| 2006/0084154 A1 | 4/2006 | Jones et al. |
| 2006/0200122 A1 | 9/2006 | Sartor et al. |
| 2006/0224146 A1 | 10/2006 | Lin |
| 2007/0021747 A1 | 1/2007 | Suslov |
| 2007/0029500 A1* | 2/2007 | Coulombe et al. ........ 250/423 F |
| 2007/0149970 A1 | 6/2007 | Schnitzler et al. |
| 2007/0213704 A1 | 9/2007 | Truckai et al. |
| 2007/0255271 A1 | 11/2007 | Dabney et al. |
| 2007/0282322 A1 | 12/2007 | Dabney et al. |
| 2008/0039832 A1 | 2/2008 | Palanker et al. |
| 2008/0108985 A1 | 5/2008 | Konesky |
| 2009/0024161 A1* | 1/2009 | Bonutti et al. ............ 606/213 |
| 2009/0048594 A1 | 2/2009 | Sartor et al. |
| 2009/0054893 A1 | 2/2009 | Sartor et al. |
| 2009/0054896 A1 | 2/2009 | Fridman et al. |
| 2009/0076505 A1 | 3/2009 | Arts |
| 2009/0216226 A1 | 8/2009 | Davison et al. |
| 2009/0275941 A1 | 11/2009 | Sartor et al. |
| 2010/0016856 A1 | 1/2010 | Platt, Jr. |
| 2010/0042094 A1 | 2/2010 | Arts |
| 2010/0069902 A1 | 3/2010 | Sartor et al. |
| 2010/0114096 A1 | 5/2010 | Podhajsky |

FOREIGN PATENT DOCUMENTS

| | | |
|---|---|---|
| DE | 4326037 | 2/1995 |
| DE | 9117019 | 4/1995 |
| DE | 19524645 | 2/1997 |
| DE | 19537897 | 3/1997 |
| DE | 9117299 | 4/2000 |
| DE | 19848784 | 5/2000 |
| DE | 29724247 | 8/2000 |
| EP | 0956827 | 11/1999 |
| FR | 1340509 | 9/1963 |
| JP | 61-159953 | 7/1986 |
| SU | 1438745 | 11/1988 |

OTHER PUBLICATIONS

U.S. Appl. No. 08/619,380, filed Mar. 21, 1996.
U.S. Appl. No. 08/621,151, filed Mar. 21, 1996.
U.S. Appl. No. 08/878,694, filed Jun. 19, 1997.
U.S. Appl. No. 09/270,856, filed Mar. 17, 1999.
U.S. Appl. No. 09/504,640, filed Feb. 16, 2000
U.S. Appl. No. 09/666,312, filed Sep. 21, 2000.
U.S. Appl. No. 12/606,672, filed Sep. 30, 2009.
U.S. Appl. No. 12/791,100, filed Jun. 1, 2010.
U.S. Appl. No. 12/845,842, filed Jul. 29, 2010.
Hernandez et al., "A Controlled Study of the Argon Beam Coagultor for Partial Nephrectomy"; The Journal of Urology, vol. 143, (May 1990) J. Urol. 143: pp. 1062-1065.
Ward et al., "A Significant New Contribution to Radical Head and Neck Surgery"; Arch Otolaryngology, Head and Neck Surg., vol. 115 pp. 921-923 (Aug. 1989).
Moore et al., "Confined Geometry Interactions of Downstream RF-Excited Atmospheric Plasma Wires", IEEE Transactions on Plasma Science, 0093-3813, (2008) pp. 1-2.
Walsh et al., "Contrasting Characteristics of Pulsed and Sinusoidal Cold Atmospheric Plasma Jets", Applied Physics Letters, 88, 171501 (2006) pp. 1-3.
Cho et al., "Coplanar ac Discharges Between Cylindrical Electrodes With a Nanoporous Alumina Dielectric: Modular Dielectric Barrier Plasma Devices", IEEE Transactions on Plasma Science, vol. 33, No. 2, (Apr. 2005) pp. 378-379.
Xu et al., "DBD Plasma Jet in Atmospheric Pressure Argon", IEEE Transactions on Plasma Science, vol. 36, No. 4, (Aug. 2008), pp. 1352-1353.
Brand et al., "Electrosurgical Debulking of Ovarian Cancer: A New Technique Using the Argon Beam Coagulator"; Gynecologic Oncology 39 pp. 115-118 (1990).
Grund et al., "Endoscopic Argon Plasma . . . Flexible Endoscopy"; Endoscopic Surgery and Allied Technologies, No. 1, vol. 2, pp. 42-46 (Feb. 1994).
Waye et al., "Endoscopic Treatment Options"; Techniques in Therapeutic Endoscopy, pp. 1.7-1.15, (1987).
B.D. Cullity, "Introduction to Magnetic Materials", University of Notre Dame; Addison-Wesley Publishing Company, Reading MA., (1972) pp. 23-28.
Yin et al., "Miniaturization of Inductively Coupled Plasma Sources", IEEE Transactions on Plasma Science, vol. 27, No. 5, (Oct. 1999) pp. 1516-1524.
Park et al., "Nanoporous Anodic Alumina Film on Glass: Improving Transparency by an Ion-Drift Process", Electrochemical and Solid-State Letters, 8 (3) (2005), pp. D5-D7.
Cho et al., "Ozone Production by Nanoporous Dielectric Barrier Glow Discharge in Atmospheric Pressure Air", Applied Physics Letters, 92, 101504, (2008) pp. 1-3.
Akitsu et al., "Plasma Sterilization Using Glow Discharge at Atmospheric Pressure", Surface & Coatings Technology 193, (2005) pp. 29-34.
Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.
Farin et al., Technology of Argon Plasma . . . Endoscopic Applications; Endoscopic Surgery and Allied Technologies, No. 1, vol. 2, pp. 71-77 (Feb. 1994).
Gupta et al., "The Potential of Pulsed Underwater Streamer Discharges as a Disinfection Technique", IEEE Transactions on Plasma Science, vol. 36, No. 4, (Aug. 2008) pp. 1621-1632.
Mark H. Mellow, "The Role of Endoscopic Laser Therapy in Gastrointestinal Neoplasms"; Advanced Therapeutic Endoscopy, pp. 17-21, (1990).

(56) References Cited

OTHER PUBLICATIONS

Silverstein et al., "Thermal Coagulation Therapy for Upper Gastrointestinal Bleeding"; Advanced Therapeutic Endoscopy, pp. 79-84, 1990.
European Search Report EP 01 10 2843.8, dated May 15, 2001.
European Search Report EP 05 00 2257, dated Jun. 1, 2005.
European Search Report EP 06 01 9572 dated Nov. 21, 2006.
European Search Report EP 07 00 4356 dated Jul. 2, 2007.
European Search Report EP 07 00 4659 dated Feb. 19, 2008.
European Search Report EP 07 00 4659—partial dated May 24, 2007.
European Search Report EP 09 00 4975 dated Sep. 11, 2009.
European Search Report EP 09 01 0519 dated Nov. 16, 2009.
European Search Report EP 09 01 0520 dated Dec. 10, 2009.
European Search Report EP 09 01 5212.5 dated Apr. 1, 2010.
European Search Report EP 09 17 1599.5 dated Mar. 16, 2010.
European Search Report EP 09 17 1600.1 dated Jan. 26, 2010.
International Search Report PCT/US98/19284, dated Jan. 14, 1999.
Supplementary European Search Report from Appl. No. EP 09 75 5799 mailed Aug. 31, 2012.

* cited by examiner

SYSTEM AND METHOD FOR REMOVING MEDICAL IMPLANTS

BACKGROUND

1. Technical Field

The present disclosure relates to plasma devices and processes for surface processing and material removal. More particularly, the disclosure relates to an apparatus and method for generating and directing plasma-generated species in a plasma device for removing medical implants.

2. Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring plasma electron temperature and electron density. In addition, adjusting spatial, temporal and temperature properties of the plasma creates specific changes to the material being irradiated by the plasma species and associated photon fluxes. Plasmas are also capable of generating photons including energetic ultraviolet photons that have sufficient energy to initiate photochemical and photocatalytic reaction paths in biological and other materials that are irradiated by the plasma photons.

SUMMARY

Plasma has broad applicability to provide alternative solutions to industrial, scientific and medical needs, especially workpiece surface processing at low temperature. Plasmas may be delivered to a workpiece, thereby affecting multiple changes in the properties of materials upon which the plasmas impinge. Plasmas have the unique ability to create large fluxes of radiation (e.g., ultraviolet), ions, photons, electrons and other excited-state (e.g., metastable) species which are suitable for performing material property changes with high spatial, material selectivity, and temporal control. The plasma may remove a distinct upper layer of a workpiece but have little or no effect on a separate underlayer of the workpiece or it may be used to selectively remove a particular tissue from a mixed tissue region or selectively remove a tissue with minimal effect to adjacent organs of different tissue type.

Various medical implants are utilized to treat cardio-vascular diseases, such as stents, indwelling catheters, meshes, pacemakers, defibrillators and the like. The devices are implanted within the cardio-vascular system (e.g., veins, ventricles, etc.). Over time, the devices need to be replaced or simply removed for a variety of reasons such as malfunction or infections at the implantation site. On occasion, the surrounding tissue tends to adhere to the implants due to continuous tissue growth around the implants. The primary method of removal of ingrown implants is removal of the surrounding tissue.

The present disclosure provides an apparatus and method of removal medical implants by modifying the tissue to prepare the tissue for removal and/or removing the surrounding tissue in a controlled manner. In one embodiment, a plasma-based catheter may be utilized to remove the tissue surrounding an implanted (e.g., defibrillator and/or pacemaker) lead. The catheter is inserted over the implanted lead to completely surround the lead. The catheter generates plasma at a distal end thereof that aids in the release of tissue along the implant as the catheter runs over the lead. The plasma plume that passes over the implant releases the tissue along the implant while minimizing the damage to surrounding tissue. In another embodiment, the catheter may be actively cooled using chilled fluids and/or gas such as saline to ensure that the plasma does not damage surrounding tissue and/or the implant. Ensuring that the implant remains intact for removal is important during such procedures since portions of the implant remaining within the tissue may cause injury to the patient. The catheter includes a controller for adjusting the rate and depth of tissue removal. The controller adjusts the energy of the plasma plume by modifying one or more of the following parameters: power, plasma feedstocks, temperature of the device (e.g., cooling).

It is also contemplated by the present disclosure that an open or laparoscopic plasma device may be used for removal of other types of implants such as meshes (e.g., hernia treatment implants) and mesh-type implants (e.g., stents and other structural implants). As stated above, plasma provides for controlled tissue removal or tissue modification, such as softening of the tissue, while minimizing collateral damage. In addition, plasma provides a wider effective range allowing for faster removal of the implant.

A method for removing a medical implant is contemplated by the present disclosure. The method includes the steps of guiding a plasma device to an implantation site. The plasma device includes a catheter, which may be a steerable catheter, having a catheter shaft. The catheter shaft includes a proximal portion and a flexible distal portion and a lumen defined therein terminating in an opening proximate a distal end thereof. The lumen is in fluid communication with an ionizable media source. The plasma device also include one or more electrodes proximate the opening and adapted to couple to a power source. The method also includes the steps of positioning the opening proximate a medical implant, supplying ionizable media to the opening, energizing the electrode to ignite the ionizable media to form a plasma plume emanating from the opening and manipulating the plasma plume relative to the medical implant to remove tissue surrounding the medical implant.

The present disclosure also provides for a plasma device. The plasma device includes a catheter, which may be a steerable catheter, having a catheter shaft. The catheter shaft includes a proximal portion and a flexible distal portion and a lumen defined therein terminating in an opening proximate a distal end of the distal portion. The lumen is in fluid communication with an ionizable media source configured to supply ionizable media thereto. The plasma device also includes one or more electrodes disposed proximate the distal portion and adapted to couple to a power source configured to energize the electrodes to ignite the ionizable media and form a plasma plume around a medical implant.

A plasma system is also provided by the present disclosure. The system includes a catheter, which may be a steerable catheter, having a catheter shaft. The catheter shaft having a proximal portion and a flexible distal portion and a lumen defined therein terminating in an opening at a distal end of the distal portion, wherein the lumen and the opening are configured to circumferentially encompass a medical implant. The catheter also includes a plurality of electrodes disposed at the distal portion. The system further includes an ionizable media source in fluid communication with the lumen and configured to supply ionizable media thereto and a power source coupled to the plurality of electrodes and configured to energize the plurality of electrodes to ignite the ionizable media at the distal portion to form a plasma plume around the medical implant.

BRIEF DESCRIPTION OF THE DRAWINGS

The accompanying drawings, which are incorporated in and constitute a part of this specification, illustrate exemplary embodiments of the disclosure and, together with a general description of the disclosure given above, and the detailed description of the embodiments given below, serve to explain the principles of the disclosure, wherein.

DETAILED DESCRIPTION

Plasmas are generated using electrical energy that is delivered as either direct current (DC) electricity or alternating current (AC) electricity at frequencies from about 0.1 hertz (Hz) to about 100 gigahertz (GHz), including radio frequency ("RF", from about 0.1 MHz to about 100 MHz) and microwave ("MW", from about 0.1 GHz to about 100 GHz) bands, using appropriate generators, electrodes, and antennas. Choice of excitation frequency, the workpiece, as well as the electrical circuit that is used to deliver electrical energy to the circuit affects many properties and requirements of the plasma. The performance of the plasma chemical generation, the delivery system and the design of the electrical excitation circuitry are interrelated, i.e., as the choices of operating voltage, frequency and current levels (as well as phase) effect the electron temperature and electron density. Further, choices of electrical excitation and plasma device hardware also determine how a given plasma system responds dynamically to the introduction of new ingredients to the host plasma gas or liquid media. The corresponding dynamic adjustment of the electrical drive, such as dynamic match networks or adjustments to voltage, current, or excitation frequency are required to maintain controlled power transfer from the electrical circuit to the plasma.

Figure 1:
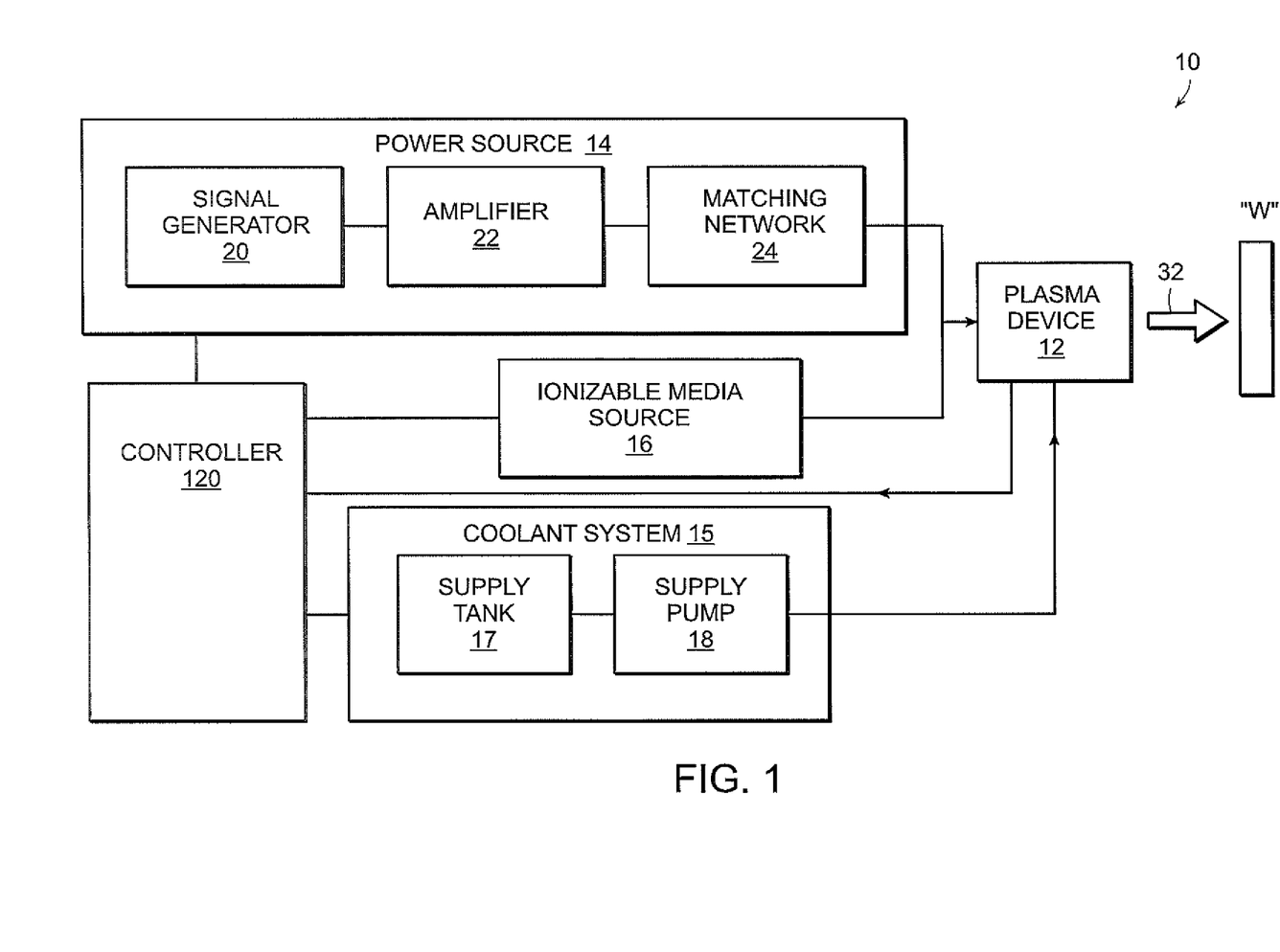
FIG. 1 is a schematic diagram of a plasma system according to the present disclosure.

Referring initially to FIG. 1, a plasma system 10 is disclosed. The system 10 includes a plasma device 12 that is coupled to a power source 14 and an ionizable media source 16. Power source 14 includes any required components for delivering power or matching impedance to plasma device 12. More particularly, the power source 14 may be any radio frequency generator or other suitable power source capable of producing power to ignite the ionizable media to generate plasma. The plasma device 12 may be utilized as an electrosurgical instrument for application of plasma to tissue and the power source 14 may be an electrosurgical generator that is adapted to supply the device 12 with electrical power at a frequency from about 0.1 MHz to about 1,000 MHz and, in another embodiment, from about 1 MHz to about 13.6 MHz. The plasma may also be ignited by using continuous or pulsed direct current (DC) electrical energy.

Power source 14 includes a signal generator 20 coupled to an amplifier 22. The signal generator 20 outputs a plurality of control signals to the amplifier 22 reflective of the desired waveform. The signal generator 20 allows for control of desired waveform parameters (e.g., frequency, duty cycle, amplitude, etc.). The amplifier 22 outputs the desired waveform at a frequency from about 0.1 MHz to about 1,000 MHz and in another illustrative embodiment from about 1 MHz to about 13.6 MHz. The power source 14 also includes a matching network 24 coupled to the amplifier 22. The matching network 24 may include one or more reactive and/or capacitive components that are configured to match the impedance of the load (e.g., plasma plume) to the power source 14 by switching the components or by frequency tuning.

The system 10 provides a flow of plasma through the device 12 to a workpiece "W" (e.g., tissue). Plasma feedstocks, which include ionizable media, are supplied by the ionizable media source 16 to the plasma device 12. During operation, the ionizable media is provided to the plasma device 12 where the plasma feedstocks are ignited to form plasma plume 32 containing ions, radicals, photons from the specific excited species and metastables that carry internal energy to drive desired chemical reactions in the workpiece "W" or at the surface thereof.

The ionizable media source 16 may include a storage tank and a pump (not explicitly shown) that is coupled to the plasma device 12. The ionizable media may be a liquid or a gas such as argon, helium, neon, krypton, xenon, radon, carbon dioxide, nitrogen, hydrogen, oxygen, etc. and their mixtures, and the like, or a liquid. These and other gases may be initially in a liquid form that is gasified during application.

The system 10 also includes a coolant system 15 for cooling the device 12 and particularly the plasma plume 32. The coolant system 15 includes a supply pump 17 and a supply tank 18. The supply pump 17 may be a peristaltic pump or any other suitable type of pump known in the art. The supply tank 17 stores the coolant fluid (e.g., saline) and, in one embodiment, may maintain the fluid at a predetermined temperature. In another embodiment, the coolant fluid may be a gas and/or a mixture of fluid and gas.

The system 10 further includes a controller 120 for adjusting the effect of the plasma plume 32. The controller 120 may be integrated with the plasma device 12 or configured as stand-alone device. The controller 120 may include buttons, activators, switches, touch screen, etc. as well as one or more outputs (e.g., display screen, LED indicators, etc.) outputting the selected plasma plume effect. The controller 120 allows the user to select the desired rate of tissue removal as well as effective dimensions of the plasma plume 32, such as area of effect and depth thereof. The controller 120 accepts user's inputs for the rate of tissue removal and effective dimensions and then signals the power source 14, the ionizable media source 16 and the coolant system 15 to adjust the power (e.g., output voltage and current), the flow rate of the ionizable media and the cooling rate (e.g., temperature and flow rate of the coolant), respectively. Adjusting one or more of these parameters allows for tailoring of plasma plume 32 to achieve the desired tissue removal rate and the effective dimensions thereof. More specifically, adjustments to power and the flow rate of the ionizable media have a direct effect on the plasma plume (e.g., increases in power and media flow provide for a larger and hotter plasma plume 32). The cooling rate dampens the effects of higher power and increases flow rates of the ionizable media and may be used to tune the tissue effects of the plasma plume 32.

Figures 2, 3:
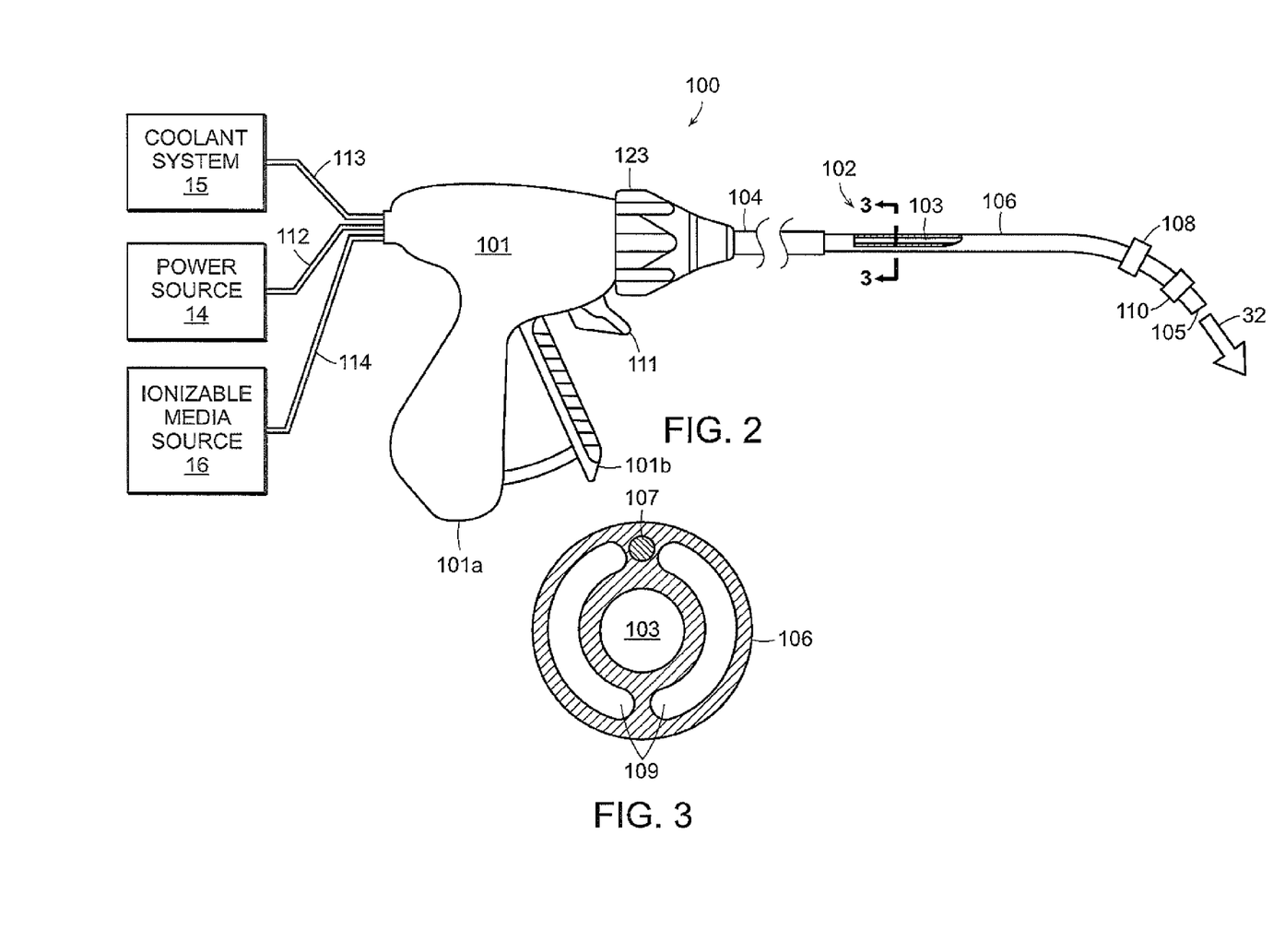
FIG. 2 is a perspective view of a plasma device according to the present disclosure.
FIG. 3 is a cross-sectional view of the plasma device of FIG. 2.

With reference to FIGS. 2 and 3, the device 12 is shown as a plasma applicator 100. The applicator 100 includes a handle 101 and a longitudinal catheter shaft 102 coupled thereto. The handle 101 includes a fixed handle 101a and a movable handle 101b that is coupled to and is movable relative to the fixed handle 101a. The shaft 102 includes a proximal portion 104 coupled to the handle 101 and a distal portion 106. The catheter shaft 102 includes a plasma lumen 103 defined therein and extending the entire length thereof and terminating in an opening 105 at distal end of the distal portion 106. The shaft 102 may have a diameter from about 5 mm to about 10 mm allowing the applicator 100 to be inserted through operating ports for application of the plasma plume 32 at the operating site during laparscopic procedures or through natural body orifices. In another embodiment, the applicator 100 may be configured for use within or accompanied by a flexible endoscope.

The catheter shaft 102 may slidably disposed within the handle 101 allowing for the longitudinal movement of the catheter shaft 102 (e.g., extension and retraction). The catheter shaft 102 may include a stop or a shoulder at a proximal end thereof that abuts a complementary shoulder or stop disposed within the handle 101 to prevent further extension of the catheter shaft 102.

The device 12 also includes controls 111 (e.g., toggle switch, trigger, etc.) coupled to the controller 120 (FIG. 1). Upon actuation, the controls 111 regulate the flow of ionizable media from the ionizable media source 16 and the precursors source 18 as well as the flow of power from the power source 14, such that the ionizable media flowing through the lumen 103 is ignited therein and is ejected from the opening 105 to form the plasma plume 32.

The handle 101 includes a rotating assembly 123 for controlling the rotational movement of the distal portion 106 about a longitudinal axis of the catheter shaft 102. The rotating assembly 123 engages one or more gears (not shown) which are attached to the catheter shaft 102. In one embodiment, the ratio of rotation of rotating assembly 123 to distal portion 106 is 1:1, however, it is contemplated that a different gearing structure may be incorporated to increase or decrease the rotational ratio depending upon a particular purpose.

In one embodiment, the distal portion 106 is configured for controlled deflection. A pull-wire 107 (FIG. 3) or another suitable actuation mechanism extends from the handle 101 at the proximal end of the applicator 100 through a lumen in the catheter shaft 102 and is fastened to the distal portion 106. The pull-wire 107 is movable from a first generally relaxed position wherein the distal portion 106 is disposed in a generally longitudinally-aligned position relative to the proximal portion 104 to a second retracted or tensed position wherein the distal portion 106 flexes (e.g., deflects) from the proximal portion 104 at a desired angle as shown in FIG. 2.

The distal portion 106 is constructed to be more flexible than the proximal portion 104, such that when the movable handle 101b is pulled back or otherwise actuated, the pull-wire bends the distal portion 106 from an undeflected position to a deflected position. In particular, the proximal portion 104 may include a wire or other support materials (not shown) therein to provide tensile strength to the catheter shaft 102 while still maintaining flexibility for maneuvering through a vascular system. The distal portion 106 is formed from a flexible biocompatible material such as polyurethane, polytetrafluoroethylene (PTFE), polyimide, and the like to allow for maneuverability thereof. In another embodiment, the catheter shaft 102 may be guided into position using a guide wire inserted into the vasculature and other anatomical lumens.

The applicator 100 includes two or more electrodes 108 and 110 disposed on the distal portion 106. The electrodes 108 and 110 may be formed from a conductive material and have a ring-like shape. The electrodes 108 and 110 may be disposed over the distal portion 106 to provide for capacitive coupling with the ionizable media. In another embodiment, the electrodes 108 and 110 may be formed as needle electrodes (e.g., pointed tip) and may be disposed within the distal portion 106. In one embodiment, the pull-wire 107 may be configured as an active or return electrode and be coupled to the power source 14. In this case, the portion of pull-wire 107 disposed within proximal portion 104 is insulated to avoid unintentional ignition and ionization of the ionizable media.

In another embodiment, the electrodes 108 and 110 may be disposed within the proximal portion 104 such that plasma is generated at the proximal section of the plasma applicator 100 and the resulting plasma plume 32 travels through the catheter shaft 102.

The electrodes 108 and 110 are coupled to conductors (not shown) that extend through the catheter shaft 102 and are connected to the power source 14 via electrical connectors 112. The catheter shaft 102 is also coupled to the ionizable media source 16 via gas tubing 114. In embodiments, the ionizable media source 16 may be a gas cartridge that may couple directly to the catheter shaft 102 via gas coupling within the fixed handle 101a. The ionizable media source 16 may include various flow sensors and controllers (e.g., valves, mass flow controllers, etc.) to control the flow of ionizable media to the applicator 100. In particular, the lumen 103 is in gaseous and/or liquid communication with the ionizable media source 16 allowing for the flow of ionizable media to flow through the catheter shaft 102 to the distal portion 106. The ionizable media is ignited by application of energy through the electrodes 108 and 110 to form plasma plume 32 exiting through the opening 105.

The applicator 100 is also coupled to a coolant system 15 via tubing 113. FIG. 3 shows a cross-sectional view of the distal portion 106 taken along the line 3-3. The applicator 100 includes the plasma lumen 103 centrally disposed therein and one or more coolant chambers 109 disposed about the centrally-located plasma lumen 103. The coolant chambers 109 are in fluid communication with the coolant system 15 allowing the coolant system 15 to circulate the coolant fluid through the distal portion 106 of the applicator 100, thereby cooling the applicator 100 and the plasma plume 32 as discussed in more detail below. Alternatively, coolant system 15 could utilize cold gas to cool applicator 100 and plasma plume 32.

Figure 4:
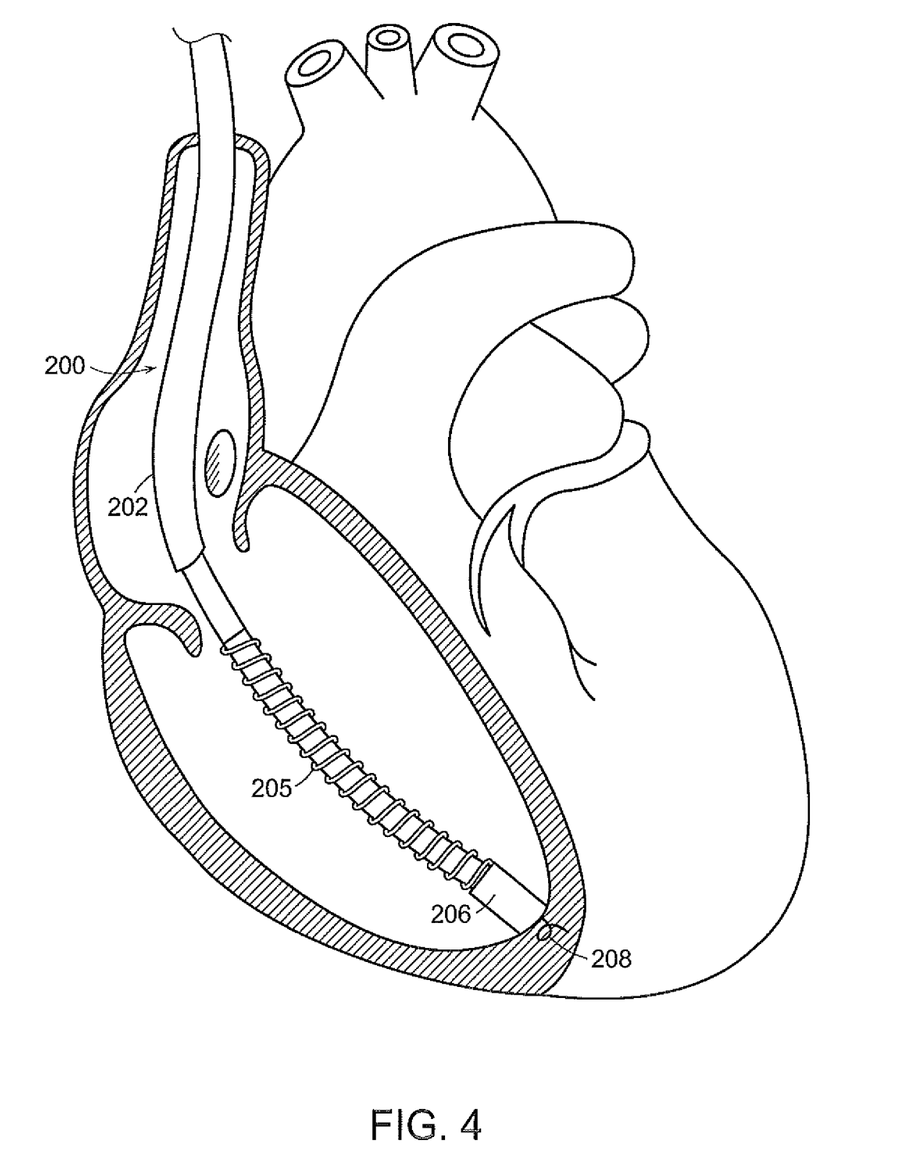
FIG. 4 is a side view of a medical implant.

FIG. 4 shows an exemplary embodiment of a medical implant implanted in the right ventricle of the heart. The medical implant is shown as a defibrillation lead 200 having an outer insulative sheath 202 disposed over an electrode 205 having an electrode head 206 at a distal end thereof. The defibrillation lead 200 also includes an attachment element 208 disposed at the electrode head 206 for securing the lead 200 to the ventricle. The lead 200 may be secured by rotation of the electrode 205, which in turn, screws the attachment element 208 into the tissue. It is envisioned that various types of medical implants may be removed using the apparatus and method according to the present disclosure and the defibrillation lead 200 is only one example of such implants.

Figure 5:
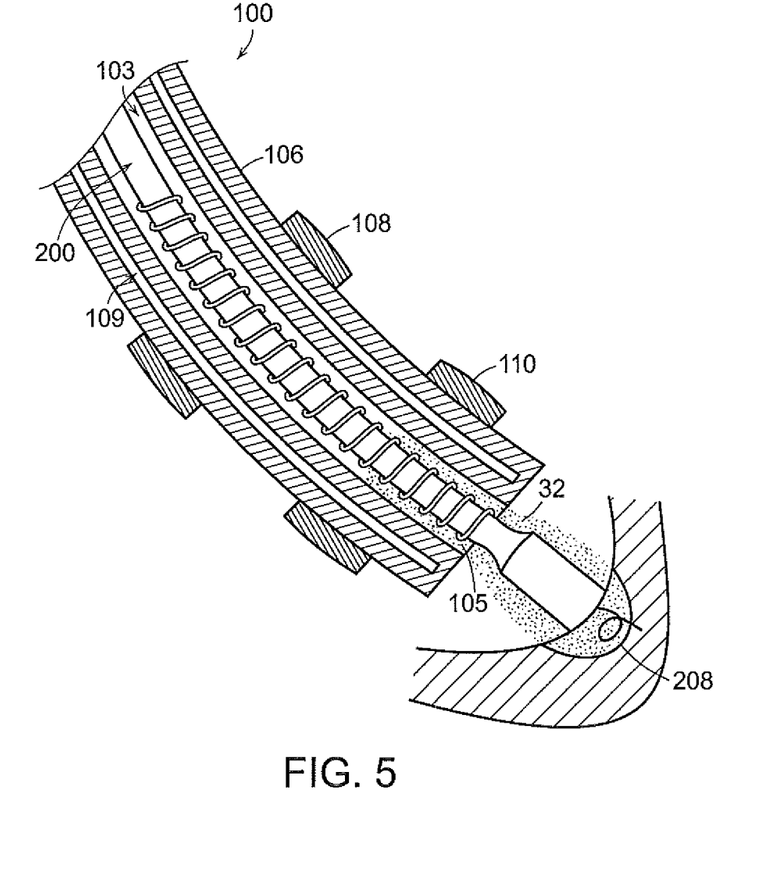
FIG. 5 is a side, cross-sectional view of the plasma device of FIG. 2 interfacing with the medical implant of FIG. 4 according to the present disclosure.
Figure 6:
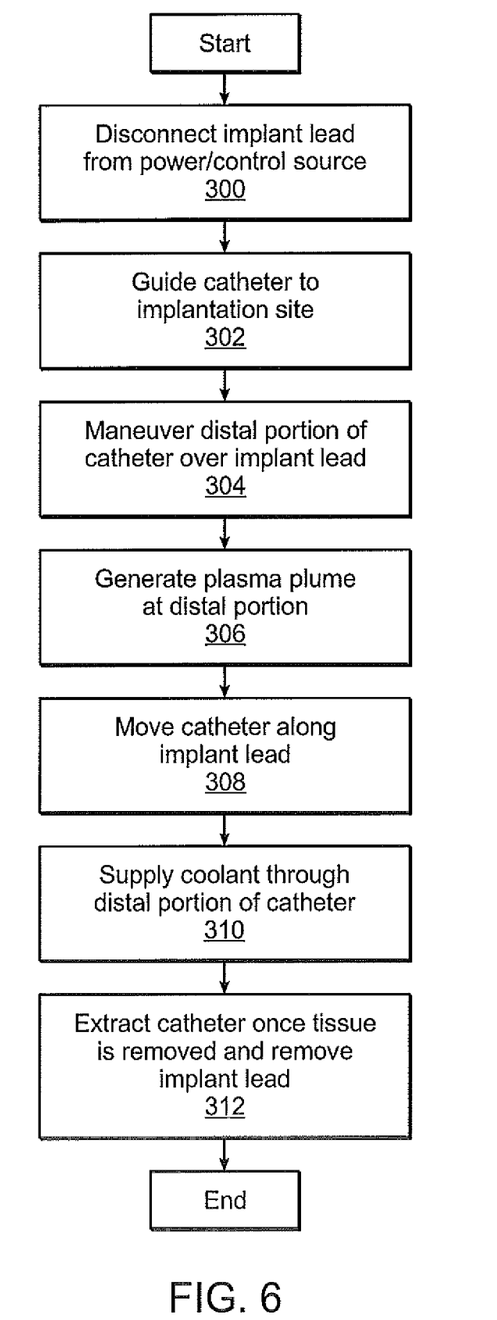
FIG. 6 is a flow chart of a method according to the present disclosure.

FIG. 5 shows the removal of the lead 200 using the applicator 100. FIG. 6 shows a flow chart of a method for removing the lead 200 and is discussed below with reference to FIG. 5. During the removal procedure, in step 300, the lead 200 is disconnected from the power and/or control source, e.g., defibrillator (not shown). This may be done by clipping the lead 200 or simply unplugging thereof from the defibrillator. In step 302, the applicator 100 is guided through the vascular system to the implantation site. The applicator 100 is advanced and is guided by the adjustment of the pull-wire 107 or by tracking over wires connected to the lead 200. In step 304, once the applicator 100 is at the implantation site, the distal portion 106 is maneuvered to cover the lead 200 as shown in FIG. 5. In other words, the proximal end of the lead 200 is inserted into the opening 105 of the applicator 100. The lumen 103 and the opening 105 are configured to circumferentially encompass the lead 200 as the distal portion 106 is moved distally along the lead 200.

In step 306, the applicator 100 is activated to generate the plasma plume 32. The user may activate the controls, e.g., inputs the rate of tissue removal and effective dimensions into controller 120, to commence the generation of plasma plume 32, which then signals the ionizable media source 16 to supply the gas through the applicator 100 and the power source 14 to energize the ionizable gas. The controller 120 accept user's inputs for the rate of tissue removal and effective dimensions and then signals the power source 14, the ionizable media source 16 and the coolant system 15 to adjust the power (e.g., output voltage and current), the flow rate of the ionizable media and the cooling rate (e.g., temperature and flow rate of the coolant), respectively. In particular, the gas is supplied through the lumen 103 and upon reaching the electrodes 108 and 110 is ignited to form the plasma plume 32.

Once the plasma plume 32 is generated, in step 308, the applicator 100 is moved distally along the lead 200 removing any tissue buildup until the applicator 100 is proximity of the tissue, such that the plasma plume 32 may reach the surface thereof as shown in FIG. 5. At this point, the plasma plume 32 is concentrated to the desired dimensions based on user's settings and removes the tissue around the attachment element 208. In another embodiment, the implant may be extracted without encompassing the lead 200 within the distal portion 106. The plasma plume 32 may be applied around the implantation site to remove the tissue and thereafter extract the implant.

In step 310, the coolant system 15 supplies coolant, if needed, to the applicator 100 through the chambers 109. The cooling rate is determined based on the selected dimensions and/or effects of the plasma plume 32. In step 312, after the tissue surrounding the attachment element 208 is removed and/or softened, the applicator 100 is extracted and the lead 200 is removed.

Figure 7:
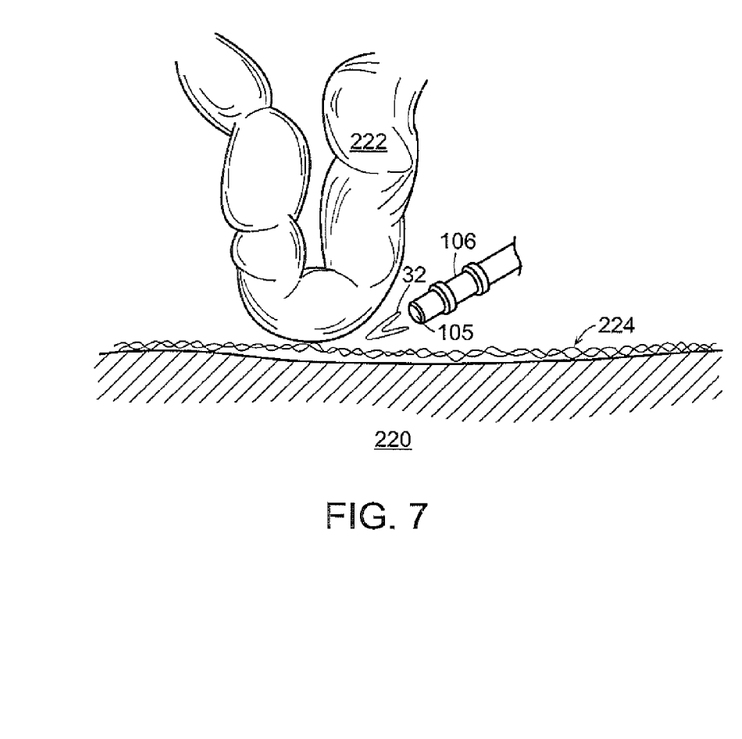
FIG. 7 is a side view of a plasma device interfacing with a mesh implanted in an abdominal wall according to the present disclosure.
Figure 8:
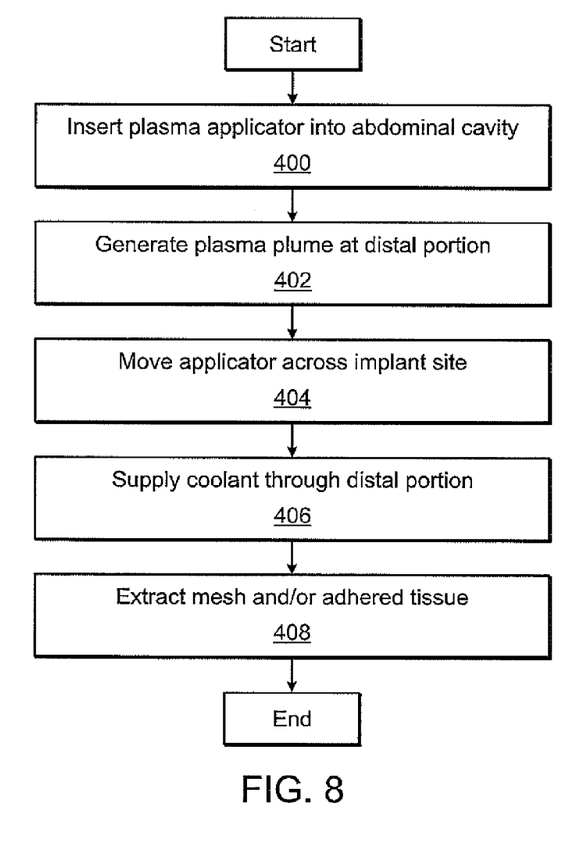
FIG. 8 is a flow chart of a method according to the present disclosure.

With reference to FIGS. 7 and 8, a method of using the applicator 100 for removing a hernia mesh 224 is discussed. FIG. 7 illustrates the mesh 224 implanted in an abdominal wall 220 and FIG. 8 illustrates a flow chart of a method for removing the mesh 224 therefrom. In certain situations, various internal organs, such as a bowel 222 may adhere to the mesh 224, requiring removal of the mesh 224 to separate the bowel 222 from the abdominal wall 220. Although the present disclosure describes a method for removing the mesh 224, the teachings may be applied to removal of other type of mesh-type implants (e.g., stents, etc.) from various types of organs (e.g., vasculature, digestive tract, etc.).

In step 400, the applicator 100 is inserted into the abdominal cavity using laparoscopic or open surgery techniques. The distal portion 106 of the applicator 100 may be deflected to direct the plasma plume 32 toward the mesh 224, and in particular, the attachment point of the bowel 222 to the abdominal wall 220. In one embodiment, the deflection may be from about 0° to about 45° with respect to a longitudinal axis defined by the shaft 102. In step 402, the ionizable media is supplied to the applicator 100 and is ignited therein to form the plasma plume 32. In one embodiment, the ionizable media may be argon, helium, oxygen, nitrogen, or a mixture of two or more thereof.

The applicator 100 is activated to generate the plasma plume 32 by activating the controls, e.g., inputs the rate of tissue removal and effective dimensions into controller 120, to commence the generation of plasma plume 32, which then signals the ionizable media source 16 to supply the gas through the applicator 100 and the power source 14 to energize the ionizable gas. The controller 120 accept user's inputs for the rate of tissue removal and effective dimensions and then signals the power source 14, the ionizable media source 16 and the coolant system 15 to adjust the power (e.g., output voltage and current), the flow rate of the ionizable media and the cooling rate (e.g., temperature and flow rate of the coolant), respectively. In particular, the gas is supplied through the lumen 103 and upon reaching the electrodes 108 and 110 is ignited to form the plasma plume 32.

In step 404, the applicator 100 is moved across the mesh 224 ensuring that the plasma plume 32 is directed at implant site, namely, the mesh 224, the abdominal wall 220 and the bowel 224. The plasma plume 32 removes and/or softens the connected tissue. In step 406, the coolant system 15 supplies coolant, if needed, to the applicator 100 through the chambers 109. The cooling rate is determined based on the selected dimensions and/or effects of the plasma plume 32. In step 408, after the tissue surrounding the mesh 224 is removed and/or softened, the applicator 100 is extracted and the mesh 224 and/or the bowel 224 are peeled from the abdominal wall 220. This prevents damage to adjacent tissue while providing for controlled separation (e.g., peeling) of the mesh 224 from the bowel 222 and/or the abdominal cavity 220. The bowel 224 may be peeled concurrently with the plasma application, once the surrounding tissue has been sufficiently softened.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method for removing a medical implant, the method comprising the steps of:
   guiding a plasma device to an implantation site, the plasma device including:
      a steerable catheter including a catheter shaft, the catheter shaft having a proximal portion and a flexible distal portion and a lumen defined therein terminating in an opening which is formed proximate a distal end thereof, the lumen being in fluid communication with an ionizable media source; and
      an active electrode and a return electrode disposed over the flexible distal portion and adapted to couple to a power source;
   positioning the catheter such that the opening is proximate a medical implant;
   encompassing the medical implant such that at least a portion of the medical implant is disposed within the lumen;
   supplying ionizable media to the opening;
   energizing the active electrode and the return electrode to capacitively couple to the ionizable media and to ignite the ionizable media to form a plasma plume emanating from the opening; and manipulating the plasma plume relative to the medical implant to remove tissue surrounding the medical implant.

2. A method according to claim 1, further comprising the step of:
   circulating a coolant fluid through the steerable catheter.

3. A method according to claim 1, further comprising the step of:
   inputting at least one tissue effect parameter into a controller to regulate at least one of rate of tissue removal and effective dimensions of the plasma plume.

4. A method according to claim 3, further comprising the step of:
   adjusting at least one of output power, flow rate of the ionizable and cooling rate in response to the at least one tissue effect parameter.

5. A method according to claim 1, wherein the plasma device of the guiding step further includes a plurality of electrodes disposed at the flexible distal portion.

6. A method according to claim 1, further comprising the step of moving the plasma device distally along the medical implant such that the medical implant is further encompassed within the lumen.

7. A method according to claim 1, further comprising the step of:
   extracting the medical implant.

* * * * *